United States Patent
Burbank et al.

(10) Patent No.: US 6,689,071 B2
(45) Date of Patent: *Feb. 10, 2004

(54) ELECTROSURGICAL BIOPSY DEVICE AND METHOD

(75) Inventors: Fred H. Burbank, San Juan Capistrano, CA (US); Paul Lubock, Laguna Niguel, CA (US); Michael L. Jones, Capistrano Beach, CA (US); Richard L. Quick, Trabuco Canyon, CA (US)

(73) Assignee: SenoRx, Inc., Aliso Viejo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/819,185

(22) Filed: Mar. 27, 2001

(65) Prior Publication Data

US 2001/0014779 A1 Aug. 16, 2001

Related U.S. Application Data

(63) Continuation of application No. 09/159,467, filed on Sep. 23, 1998, now Pat. No. 6,261,241, which is a continuation-in-part of application No. 09/057,303, filed on Apr. 8, 1998, now Pat. No. 6,331,166.
(60) Provisional application No. 60/076,973, filed on Mar. 3, 1998.

(51) Int. Cl.⁷ .............................................. A61B 10/00
(52) U.S. Cl. .................. 600/564; 600/567; 606/45; 606/167
(58) Field of Search .................................. 600/373, 393, 600/562, 564, 568, 567; 604/22, 164.01, 164.11; 606/37, 39, 41, 45–52, 167, 170; 607/115, 116

(56) References Cited

U.S. PATENT DOCUMENTS

| 2,032,860 A | 3/1936 | Wappler et al. |
| 3,805,791 A | 4/1974 | Seuberth et al. |

(List continued on next page.)

FOREIGN PATENT DOCUMENTS

| DE | 19528440 A1 | 8/1995 |
| EP | 0472368 A2 | 8/1991 |

(List continued on next page.)

OTHER PUBLICATIONS

Sterotactic Breast Biopsy: Its History, Its Present, and Its Future, F. Burbank, M.D., *The American Surgeon*, Feb. 1996, vol. 62, pp. 128–150.

(List continued on next page.)

*Primary Examiner*—Max F. Hindenburg
*Assistant Examiner*—Charles Marmor, II
(74) *Attorney, Agent, or Firm*—Edward J. Lynch; Duane Morris LLP (57) ABSTRACT

An electrosurgical biopsy device includes a stylet with a shaft, a head and an ablation element, a cannula with a distal end opening and an ablation element adjacent the opening, and optionally a base. The stylet shaft is movably disposed through the cannula. A translation mechanism controllably moves (a) the stylet between the withdrawn and extended positions and (b) the cannula between a proximal position and a distal position relative to the base. The stylet ablation element may be activated and the stylet and cannula pushed through skin and tissue until the stylet head is adjacent a targeted tissue mass. The stylet may then be extended so that its head penetrates the tissue mass. The cannula ablation element may then be activated, and the cannula pushed through the tissue mass toward the stylet head, cutting and capturing a tissue specimen within the distal end of the cannula.

13 Claims, 7 Drawing Sheets

U.S. PATENT DOCUMENTS

| | | |
|---|---|---|
| 3,955,578 A | 5/1976 | Chamness et al. |
| 4,202,338 A | 5/1980 | Bitrolf |
| 4,243,048 A | 1/1981 | Griffin .................. 600/567 |
| 4,294,254 A | 10/1981 | Chamness |
| 4,311,143 A | 1/1982 | Komiya |
| 4,362,160 A | 12/1982 | Hiltebrandt .................. 606/46 |
| 4,503,855 A | 3/1985 | Maslanka |
| 4,565,200 A | 1/1986 | Cosman .................. 606/50 |
| 4,576,162 A | 3/1986 | McCorkle |
| 4,638,802 A | 1/1987 | Okada |
| 4,718,419 A | 1/1988 | Okada |
| 4,724,836 A | 2/1988 | Okada |
| 5,007,908 A | 4/1991 | Rydell |
| 5,024,617 A | 6/1991 | Karpiel |
| 5,035,696 A | 7/1991 | Rydell |
| 5,047,027 A | 9/1991 | Rydell .................. 606/48 |
| 5,064,424 A | 11/1991 | Bitrolf .................. 606/46 |
| 5,066,295 A | 11/1991 | Kozak et al. |
| 5,078,716 A | 1/1992 | Doll |
| 5,080,660 A | 1/1992 | Buelna |
| 5,133,359 A | 7/1992 | Kedem .................. 600/567 |
| RE34,056 E | 9/1992 | Lindgren et al. .......... 600/567 |
| 5,158,561 A | 10/1992 | Rydell et al. |
| 5,163,938 A | 11/1992 | Kambara et al. |
| 5,196,007 A | 3/1993 | Ellman et al. |
| 5,201,732 A | 4/1993 | Parins et al. |
| 5,201,741 A | 4/1993 | Dulebohn |
| 5,207,686 A | 5/1993 | Dolgin |
| 5,224,488 A | 7/1993 | Neuffer |
| 5,281,218 A | 1/1994 | Imran .................. 606/21 |
| 5,312,400 A | 5/1994 | Bales et al. |
| 5,318,564 A | 6/1994 | Eggers |
| 5,323,768 A | 6/1994 | Saito et al. |
| 5,324,288 A | 6/1994 | Billings et al. .......... 606/45 |
| 5,335,671 A | 8/1994 | Clement |
| 5,344,420 A | 9/1994 | Hilal et al. |
| 5,376,094 A | 12/1994 | Kline |
| 5,380,321 A | 1/1995 | Yoon |
| 5,395,312 A | 3/1995 | Desai |
| 5,415,656 A | 5/1995 | Tihon et al. .................. 606/46 |
| 5,417,687 A | 5/1995 | Nardella et al. .......... 606/32 |
| 5,417,697 A | 5/1995 | Wilk et al. |
| 5,423,809 A | 6/1995 | Klicek .................. 606/38 |
| 5,423,814 A | 6/1995 | Zhu et al. |
| 5,431,649 A | 7/1995 | Mulier et al. .......... 606/41 |
| 5,437,665 A | 8/1995 | Munro |
| 5,441,503 A | 8/1995 | Considine et al. |
| 5,462,553 A | 10/1995 | Dolgin |
| 5,470,308 A | 11/1995 | Edwards et al. .......... 604/22 |
| 5,484,436 A | 1/1996 | Eggers et al. |
| 5,501,654 A | 3/1996 | Failla et al. |
| 5,526,822 A | 6/1996 | Burbank et al. .......... 600/567 |
| 5,542,948 A | 8/1996 | Weaver et al. |
| 5,611,803 A | 3/1997 | Heaven et al. |
| 5,643,282 A | 7/1997 | Kieturakis |
| 5,649,547 A | 7/1997 | Ritchart et al. .......... 600/567 |
| 5,665,085 A | 9/1997 | Nardella |
| 5,674,184 A | 10/1997 | Hassler, Jr. |
| 5,687,739 A | 11/1997 | McPherson et al. ........ 600/567 |
| 5,715,825 A | 2/1998 | Crowley .................. 600/462 |
| 5,741,225 A | 4/1998 | Lax et al. .................. 604/22 |
| 5,769,086 A | 6/1998 | Richart et al. |
| 5,782,775 A | 7/1998 | Milliman et al. .......... 600/567 |
| 5,794,626 A | 8/1998 | Kieturakis .................. 600/567 |
| 5,797,907 A | 8/1998 | Clement .................. 606/49 |
| 5,902,272 A | 5/1999 | Eggers et al. .................. 604/114 |
| 5,925,044 A | 7/1999 | Hofmann et al. .......... 606/45 |
| 5,941,869 A * | 8/1999 | Patterson et al. .......... 604/508 |
| 5,947,964 A | 9/1999 | Eggers et al. .................. 606/41 |
| 6,261,241 B1 * | 7/2001 | Burbank et al. .......... 600/564 |
| 6,331,166 B1 * | 12/2001 | Burbank et al. .......... 600/567 |

FOREIGN PATENT DOCUMENTS

| | | |
|---|---|---|
| EP | 95/02371 | 1/1995 |
| EP | 95/023701 | 1/1995 |
| EP | 0 667 126 A1 | 8/1995 |
| GB | 2311468 A | 2/1997 |
| WO | WO 93 13718 | 7/1993 |
| WO | WO 98 08441 | 3/1998 |
| WO | WO 00 16697 | 3/2000 |

OTHER PUBLICATIONS

Percutaneous Biopsy Techniques, Timothy J. Micklos, *Manual of Oncologic Therapeutics*, (1989/1990), pp. 39–42.

Coaxial Core Needle Biopsy Under Mammographic Guidance: Indications and Applications, Whitman et al., AJR:171, Jul. 1998, pp. 67–70.

Armstrong, J.S. et al., "Differential marking of excision planes in screened breast lesions by organically coloured gelantins [see comments]", *Journal of Clinical Pathology*, (1990 Jul.), 43(7) 604–7, XP000971447 abstract; tables 1&2.

"The Loop Electrode: a New Device for US–Guided for US–Guided Interstitial Tissue Ablation Using Radio Frequency Electrosurgery –An Animal Study", 1996 Blackwell Science Ltd., *Min Incas Ther & Allied Technol* pp. 5, 511–516.

* cited by examiner

FIG. 15

ELECTROSURGICAL BIOPSY DEVICE AND METHOD

CROSS-REFERENCE TO RELATED APPLICATIONS

This application is a continuation of ELECTROSURGICAL BIOPSY DEVICE AND METHOD, Ser. No. 09/159,467, filed Sep. 23, 1998, by Burbank, Lubock, Jones and Quick, now U.S. Pat. No. 6,261,241, which is a continuation-in-part of U.S. application Ser. No. 09/057,303, titled "Breast Biopsy System and Methods" filed Apr. 8, 1998, by Burbank, Jones and Lubock, now U.S. Pat. No. 6,331,166 which is a non-provisional application of provisional patent application Ser. No. 60/076,973, filed Mar. 3, 1998.

FEDERALLY SPONSORED RESEARCH OR DEVELOPMENT

Not Applicable

BACKGROUND OF THE INVENTION

The present invention relates to devices and methods for removing a sample of tissue from a human or animal. In particular, the present invention pertains to devices and methods for conducting a biopsy to remove a sample or specimen of a tumor or lesion for examination and analysis.

In diagnosing and treating certain medical conditions, such as potentially cancerous tumors, it may be desirable to extract from a portion of suspicious tissue, such as a tumor, a specimen of the suspicious tissue for detailed examination and analysis. The process of removing such a specimen of tissue is referred to as a biopsy.

In many instances, the suspicious tissue to be examined is inside the patient's body. For example, the suspicious tissue may be a tumor inside a human breast. To minimize surgical intrusion into the body, it is desirable to be able to insert a small instrument into the body for extracting a portion of the suspicious tissue.

Different types of instruments and procedures have been developed for conducting biopsies to extract a tissue specimen for analysis. One device that has been developed is the fine needle aspirator. This device comprises a hollow needle, the end of which is sharpened. The needle is inserted into the suspicious tissue so that individual cells or clusters of cells of the tissue lodge inside the hollow core of the needle. The needle is then extracted from the patient, and the cells and fluid removed from the needle for a cytological examination. In certain circumstances, however, it may be desirable to extract portions of tissue for a histological examination, a procedure that is not typically feasible using a fine needle aspirator.

Another type of tissue-sampling device for biopsies is exemplified by the device described in U.S. Pat. No. Re. 34,056—Lindgren et al. This type of device includes a forward stylet, which includes at its distal end a sharpened cutting surface. The stylet may be, for example, a needle sized between 12 and 20 gauge. Behind the sharpened cutting end of the stylet, along the shaft thereof, is a groove. A hollow cannula surrounds the stylet, and has its distal end sharpened to form a fine cutting edge. A mechanism is provided to move the stylet and the cannula forward separately. For example, springs may be used for this purpose. Preferably, the stylet and the cannula are moved forward rapidly so that the sharpened ends thereof may efficiently cut the tissue. In operation, the operator of this type of device first causes the stylet to be pushed forward through the tumor or suspect tissue. After the distal end of the stylet has passed through the suspect tissue, a portion of the tissue surrounding the stylet partially fills the groove on the shaft of the stylet. The cannula is then pushed forward so that the sharpened distal end of the cannula cuts off the portion of the tissue that has filled the groove on the shaft of the stylet, and encloses that tissue. The entire device may then be removed from the patient's body, and the tissue trapped in the cannula removed for examination and analysis.

U.S. Pat. No. 5,526,822—Burbank et al. discloses another type of biopsy device that includes the ability to apply a vacuum to the groove in the stylet. This vacuum assists in drawing tissue into the groove, ensuring that a more substantial portion of tissue is severed by the cutting cannula. Using such a system, it is in some cases possible to use a relatively large stylet (e.g., a 7 to 14 gauge needle) to obtain a relatively large tissue sample.

All of the above-described systems use knife edges to a cut the tissue. The cutting edge must remain extremely sharp, so that it cuts the tissue cleanly. Moreover, the stylet and the cannula cutter must be propelled forward rapidly to provide a clean cut through the tissue. Elaborate mechanisms are typically employed to provide the rapid forward movement. Because the knife edges move rapidly, however, there is limited time for tissue to fill the groove on the stylet. Therefore, the system sometimes obtains a smaller sample than would be ideal. In addition, variations in tissue density and anatomy may cause the stylet to deflect from its ideal position in relation to the tissue to be penetrated.

Electrosurgical techniques have been used in a variety of circumstances, including certain types of biopsies. In electrosurgery, high frequency electrical energy is applied through a primary electrode to tissue. The electrical energy flows through the tissue to a return electrode. The tissue adjacent to the primary electrode is ablated, to form an opening in the tissue. The return electrode in monopolar electrosurgery may be a large electrode placed on the exterior of the patient's body at a point remote from the primary electrode. In bipolar electrosurgery, the return electrode may be a smaller electrode positioned somewhat near the primary electrode. An exemplary biopsy instrument using electrosurgical techniques is described in International Publication No. WO 98/08441.

SUMMARY OF THE INVENTION

The present invention, in one aspect, is a novel electrosurgical tissue sampling device, or biopsy device, including a novel electrosurgical stylet. In another aspect, the present invention is a method of using the novel biopsy device to obtain a tissue specimen.

The novel stylet of the present invention includes a shaft that has a proximal end and a distal end. At the distal end of the stylet shaft is a substantially hemispherical head. A stylet electrode extends distally from the stylet head. The stylet electrode may be activated with radio frequency (RF) electrical energy to ablate the tissue adjacent the stylet electrode. A cannula that cooperates with the stylet also has a proximal end and a distal end. An opening is formed at the distal end of the cannula. The distal end of the cannula may be selectively separated from the stylet, or may abut the stylet to close the opening at the distal end of the cannula. Also at the distal end of the cannula is another electrode that also may be activated with radio-frequency electrical energy to ablate the tissue adjacent the distal end of the cannula.

The system may be monopolar, in which the return electrical path is provided by a return electrode attached to the patient's body remote from the device. Alternatively, the system may be bipolar, in which the return electrical path is provided by a return electrode on the device itself. The same return electrical path may be used for both the electrode on the stylet and the electrode on the cannula.

In accordance with the method of the present invention, the electrode on the head of the stylet is energized. With the stylet in a withdrawn position abutting against the distal end of the cannula, the stylet and the cannula are pushed through the skin and the underlying tissue, while applying an RF current, until the head of the stylet is adjacent a targeted tissue mass (e.g., a lesion or tumor). Next, the stylet is extended distally from the distal end of the cannula so that its head penetrates the targeted tissue mass, whereby the stylet head and the distal end of the cannula are on opposite sides of the tissue mass. The electrode at the distal end of the cannula is then energized, and the cannula is pushed through the tissue mass toward the stylet head, thereby cutting a "core" through the tissue mass that is captured as a tissue specimen within the distal end of the cannula. The cannula and the stylet are then removed from the patient's body. After the cannula and the stylet have been removed, they may be separated from one another, and the tissue specimen enclosed within the cannula may be removed and examined.

DETAILED DESCRIPTION OF THE INVENTION

Figures 1, 1A:
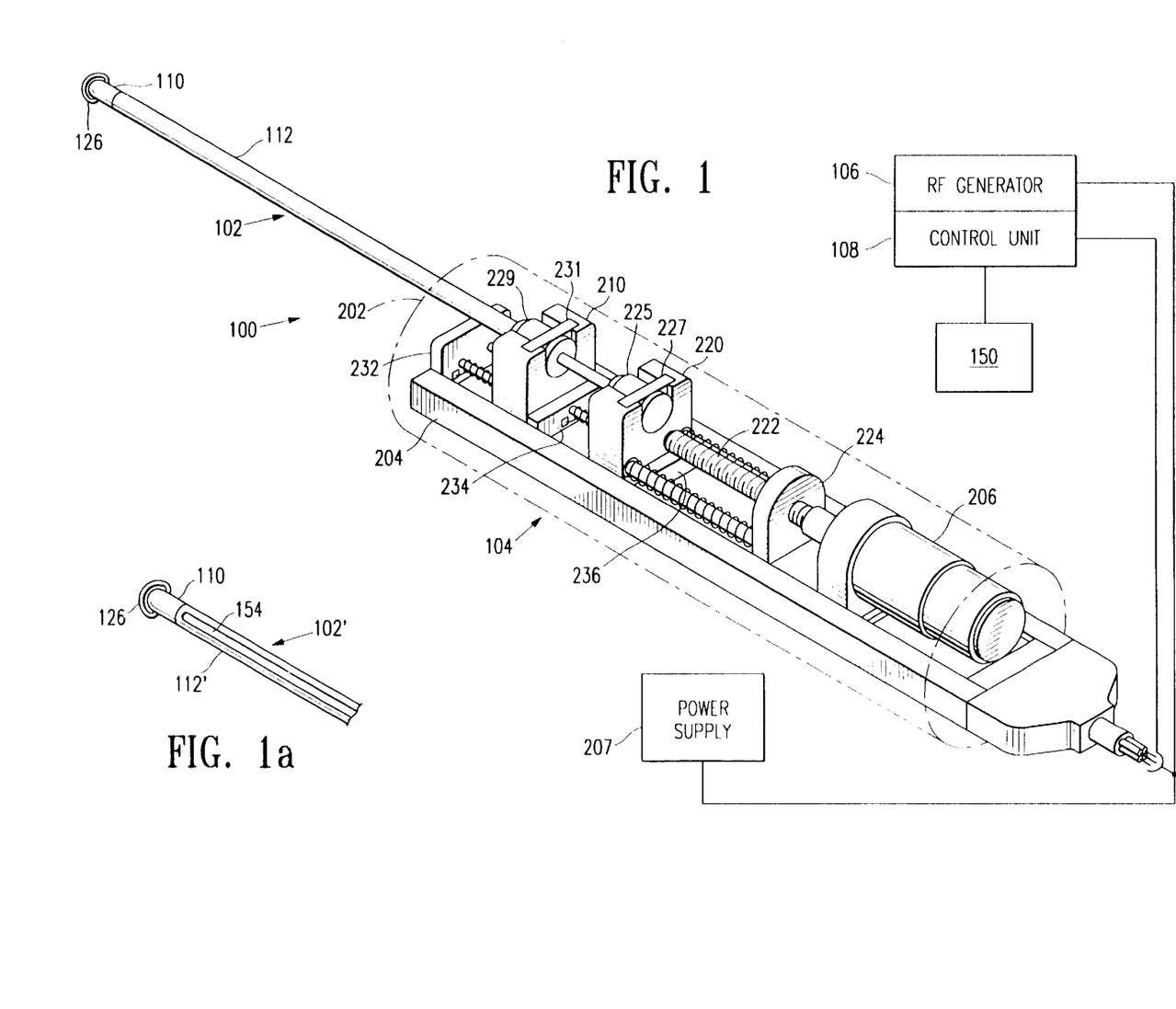
FIG. 1 is a perspective view of a preferred embodiment of a biopsy device constructed in accordance with the present invention.
FIG. 1A is a perspective view of a portion of the cannula and stylet of a modified form of the preferred embodiment of the biopsy device.
Figure 2:
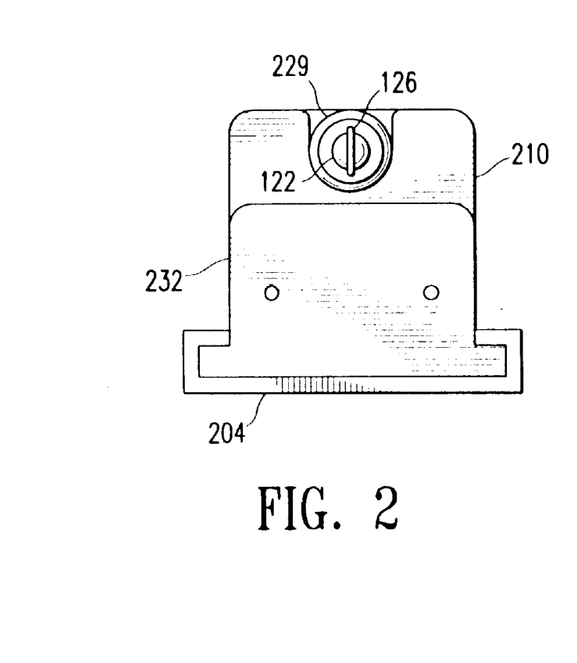
FIG. 2 is a distal end view of the device illustrated in FIG. 1, taken from the left side of FIG. 1.

Referring first to FIG. 1, a particular preferred embodiment of a biopsy device 100, constructed in accordance with the present invention, is illustrated. The biopsy device 100 includes a probe 102, a base unit 104, an energy source, such as a radio-frequency generator 106, and a control unit 108.

The probe 102 includes a stylet 110 and a cannula 112. The stylet 110 electrosurgically separates tissue through the use of an electrical current activated at high frequency, such as a frequency in the radio frequency range. The stylet 110, when electrically activated, ablates tissue adjacent its electrically active components.

Figure 3:
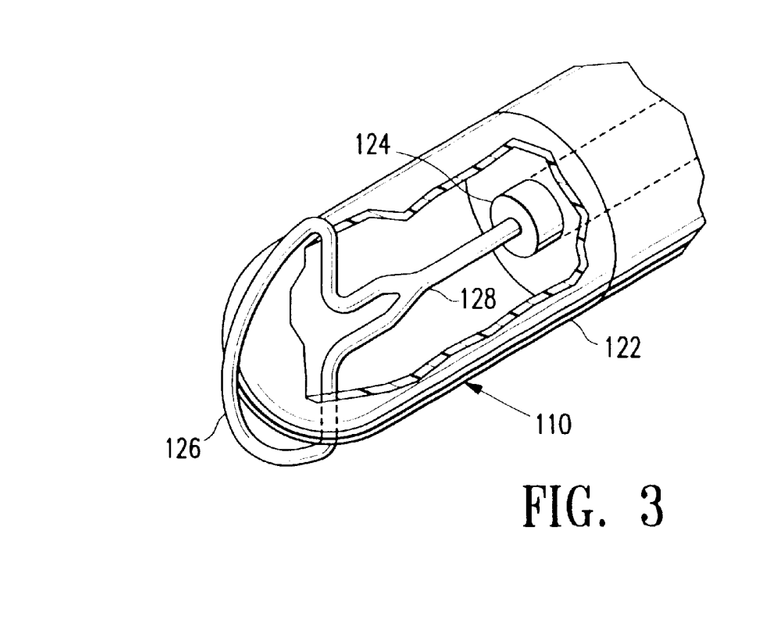
FIG. 3 is a perspective view, partially broken away, of a preferred embodiment of an electrosurgical stylet constructed in accordance with an aspect of the present invention, and incorporated in the device illustrated in FIG. 1.

The stylet 110, comprising an aspect of the present invention, is shown in FIG. 3. The stylet 110 includes a stylet head 122 having a substantially cylindrical body with a substantially hemispherical surface at the distal end of the stylet head 122. The stylet head 122 is formed of an electrically insulating material, such as a plastic. The stylet head 122 is attached to the distal end of a stylet shaft 124, which is also formed of an electrically insulating material. The stylet shaft 124 may have a central longitudinal bore through it, preferably along the longitudinal axis of the shaft 124.

A conductive metal stylet electrode 126 protrudes distally from the stylet head 122. In the illustrated embodiment, the stylet electrode 126 is formed of an arcuate length of electrical conductor that protrudes from diametrically opposite sides of the stylet head 122, and extends over the hemispherical distal end surface of the stylet head 122. The radius of curvature for the stylet electrode 126 is substantially coplanar with the longitudinal axis of the stylet shaft 124. The stylet electrode 126 forms a first tissue ablation element for electrosurgically separating tissue so as to create an incision.

For the purposes of the present description of the invention, the term "ablation", as used in this specification, is defined as the process of creating an incision by vaporizing tissue. The preferred embodiment described herein uses electrical energy in the radio frequency range for the ablation process. However, tissue ablation may also be accomplished with other energy sources, such as microwaves or ultrasound. In such cases, the configuration of the ablation elements may differ from the ablation electrodes described hereinbelow. The energy supply and control system may differ as well. The appropriate variations and modifications in these components to accommodate the alternative energy sources will suggest themselves to those skilled in the pertinent arts.

The stylet electrode 126 merges into a single stylet electrical conductor 128 inside the stylet head 122. The single stylet electrical conductor 128 extends through the central bore in the stylet shaft 124. The stylet conductor 128 is electrically connected with both ends of the stylet electrode 126.

Figure 16:
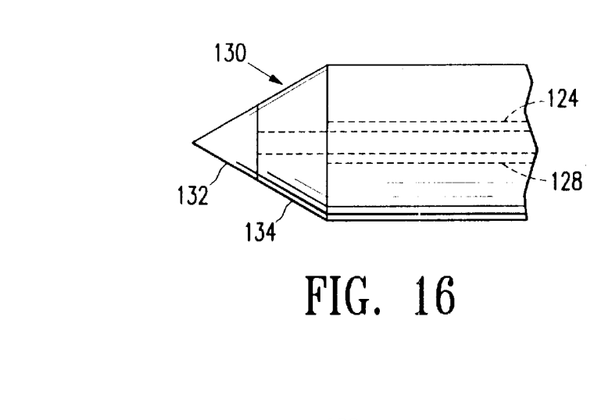
FIG. 16 is a side elevational view of an alternative embodiment of the electrosurgical stylet that may be incorporated in the biopsy device of the present invention.

An alternative embodiment of the stylet head is illustrated in FIG. 16. The embodiment illustrated in FIG. 16 includes a conical head 130 that has an electrically conductive apex portion 132 that forms the stylet electrode. The apex portion is secured to the distal end of an insulative, frustrum-shaped base portion 134. The conical stylet electrode 132, which forms the stylet tissue ablation element, is in electrical contact with the stylet conductor 128 (as described above with reference to FIG. 3).

The cannula 112 is formed of an elongated hollow outer tube 140 (FIGS. 12, 13, and 14) that has a distal end and a proximal end.

Preferably, the longitudinal axis of the cannula 112 coincides with the longitudinal axis of the stylet shaft 124. The outer tube 140 of the cannula 112 is formed of an electrically nonconductive or insulating material, such as plastic, and may be formed by extrusion. For example, the outer tube 140 of the cannula may be formed of a polyimide. The outer surface of the cannula tube 140 may be coated with TEFLON® (polytetrafluoroethylene) or similar low-friction polymeric material to reduce sticking between the surface and the surrounding tissue.

At the distal end of the cannula 112 is a cannula electrode 142 forming a second tissue ablation element. The cannula electrode 142 may be formed of the distal end of a tubular conductor 144 extending along the length of the cannula 112, inside the outer tube 140.

An electrically insulating inner sleeve 146 may cover the inner surface of the tubular conductor 144. The inner cannula sleeve 146 may also be formed by extrusion of a polyimide. The inner surface of the inner cannula sleeve 146 may be coated with a low-friction polymeric material, such as TEFLON®. The inner insulating sleeve 146 is spaced from the stylet shaft 124 to form an annular passage 148 that is open at the distal end of the cannula 112. The annular passage 148 receives tissue samples that are severed by the cannula electrode 142, as described below.

Figure 13:
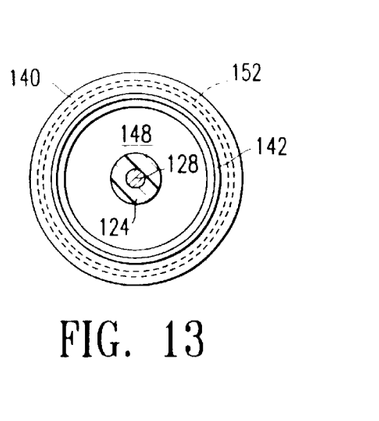
FIG. 13 is a view taken along line 13—13 of FIG. 5, showing a distal end view of the cannula, and a cross-sectional view of the stylet shaft.
Figure 14:
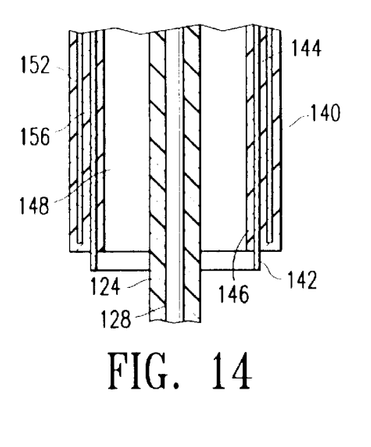
FIG. 14 is a cross-sectional view taken along line 14—14 of FIG. 12.

In a bipolar configuration for the probe, described below, the cannula 112 will include other elements 152, 156, shown in FIGS. 12, 13, and 14. These other elements, described below, are not incorporated in the monopolar configuration.

The stylet 110 and the cannula 112 may be moved relative one another along their common longitudinal axis. For example, the stylet 110 may be moved relative to the cannula 112 between an extended position in which the distal end of the stylet shaft 124 and the stylet head 122 are separated from the distal end of the cannula 112, and a withdrawn position in which the stylet head 122 abuts or is in close proximity to the distal end of the cannula 112.

Those familiar with electrosurgical techniques will understand that when a high frequency electrical current is applied to a primary electrode, such as the stylet electrode 126, and the primary electrode is exposed to tissue, the tissue adjacent the primary electrode is ablated. To perform such electrosurgery, a return electrical path through the tissue is required, to close the electrical circuit.

An electrosurgical device may be either monopolar or bipolar. With a monopolar device, the return electrical path is provided through a return electrode that may be a grounded contact pad that is applied to the exterior of the patient's body at a point remote from where the primary electrode is placed in the body. With a bipolar device, the return electrical path is provided from the primary or ablation electrode through a return electrode that is located relatively near the primary electrode. The bipolar return electrode is contained on the same instrument body as the primary electrode. Although parts of the present invention are described with reference to a monopolar configuration, and parts are described with reference to a bipolar configuration, those skilled in the art will recognize how the device may be implemented in either configuration.

In the monopolar configuration of the biopsy device illustrated in FIG. 1, a patient return pad 150 is attached to the patient's body, and is in electrical contact with the RF generator 106. The patient return pad 150 forms a return electrode for the energy delivered by the RF generator 106 to the stylet electrode 126 and the cannula electrode 142. In the monopolar configuration, the annular conductor 144 that terminates in the cannula electrode 142 is disposed between the external insulating layer of the tube 140, and the inner insulating sleeve 146.

A probe 102' used in the bipolar configuration of the biopsy device in accordance with the present invention is shown in FIG. 1A. In the bipolar configuration, the return electrical path is provided through a conductor contained within a bipolar cannula 112'. Referring to FIGS. 12, 13, 14, and 1A, the additional elements of the bipolar cannula 112' are shown. A conductive layer 152 is contained just under the outer tube 140, and forms a return path electrode. A pair of diametrically-opposed longitudinal side openings or slots 154 (one of which is shown in FIG. 1A) are provided in the outer tube 140. These side openings 154 may extend longitudinally along a substantial portion of the length of the cannula 112'. Through these openings 154 in the outer tube 140, the conductive layer 152 forming the return path electrode is exposed to the environment surrounding the cannula 112'. Thus, when the probe 102' (FIG. 1A) is inserted into a patient's tissue, the return electrode 140 is in contact with the tissue, and electrical current may flow through the tissue from the stylet electrode 126 and the cannula electrode 142 to the return electrode 152. The return electrode is advantageously electrically connected to ground potential.

Figure 12:
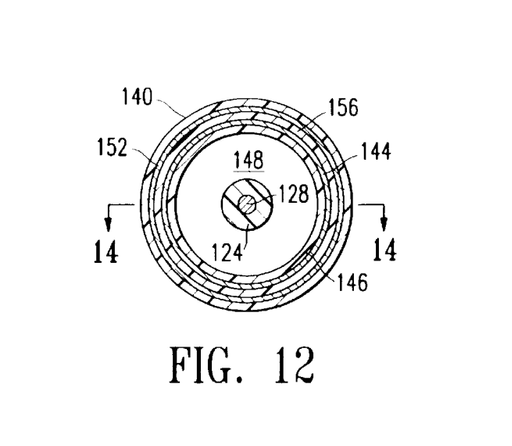
FIG. 12 is a cross-sectional view of the cannula and stylet, taken along line 12—12 of FIG. 6.

Referring now particularly to FIG. 12, the annular cannula conductor 144 in a bipolar implementation is spaced from the return path electrode 152 by an insulating layer 156 of non-conductive material, such as plastic. The insulating layer 156 electrically isolates the return path electrode 152 from the cannula conductor 144.

When activated with a current oscillating at high frequency (such as in the radio frequency range), the cannula electrode 142 ablates tissue adjacent to the cannula electrode. As with the stylet electrode 126, the operation may be either monopolar or bipolar. For operation in accordance with a bipolar technique, the same return electrode 152 used with the stylet electrode 126 may also be used in conjunction with the cannula electrode 142. However, those skilled in the art, taking the teaching provided herein, will also recognize that alternative electrical return paths may be provided.

Figure 17:
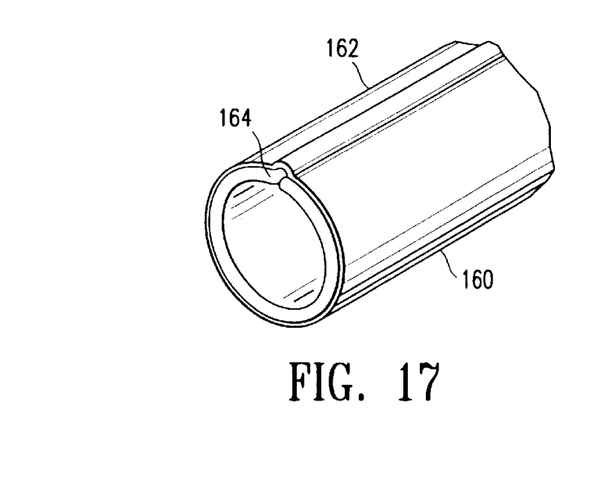
FIG. 17 is a perspective view of an alternative embodiment of the cannula portion of the biopsy device of the present invention.

An alternative embodiment of the cannula is illustrated in FIG. 17. This particular alternative embodiment is illustrated as a monopolar device. However, those skilled in the art will recognize that the illustrated embodiment may be modified to add a return electrode to implement a bipolar embodiment. In the alternative embodiment illustrated in FIG. 17, the cannula is formed of a cannula body 160. A cannula conduit 162 extends along the length of the cannula body 160. A length of conductor extends through the cannula conduit 162, and is formed into a substantially circular cannula electrode 164 that coincides with the distal end of the cannula body 160. Those skilled in the art will readily recognize that other configurations may be used to form the cannula electrode at the distal end of the cannula. For example, the cannula conduit 162 may be formed as a groove cut along the length of the cannula body 160. Similarly, the cannula conduit 162 may be formed on the interior surface of the cannula body 160.

An energy source, such as the radio-frequency generator 106, generates the electrical current required for application to the stylet electrode 126 and the cannula electrode 142. The design, construction, and operation of such a generator and control unit are conventional and well-understood by those familiar with electrosurgery technology.

The base unit 104 controls the position and movement of the stylet 110, the cannula 112, and the application of the electrical energy generated by the generator and control unit 106 to the stylet electrode 126 and the cannula electrode 142. The base unit 104 permits the cannula 112 and stylet 110 to be moved together, and also to be moved separately. For example, the probe 102, including both the stylet 110 and the cannula 112, may be moved between an extended position relative to the base unit 104 in which the distal end of the stylet 110 and the distal end of the cannula 112 are relatively farther from the base unit 104, and a withdrawn position in which the distal end of the stylet 110 and the distal end of the cannula 112 are relatively closer to the base unit 104. Furthermore, the base unit 104 may extend the stylet 110 between an extended position relative to the cannula 112, and a withdrawn position relative to the cannula 112.

The base unit 104 may be enclosed in a housing 202 (shown in phantom lines in FIG. 1). The housing 202 protects the internal elements of the device. The housing 202 may be substantially sealed to protect the internal elements of the base unit 104 from contamination during use of the stylet 110 and cannula 112 during a biopsy procedure. However, the housing 202 may be selectively removable, or have an access panel (not shown) provided to allow access to certain elements within the base unit 104. In addition, the housing 202 may be shaped to facilitate hand holding of the device, or it may be configured to be attached to other devices (not shown) for holding the biopsy device in the proper position for conducting the biopsy procedure.

Referring now to FIGS. 1, 4, 5, and 6, the base unit 104 includes a base 204 to which is fixed an electric motor 206 (preferably a DC motor powered by a power supply 207). The motor 206 is employed for moving the stylet 110 and the cannula 112 relative to the base unit 104. A cannula carrier 210 is slidably mounted on the base 204. The cannula 112 has a proximal end that is attached to a cannula carrier 210. The cannula carrier 210 translates the cannula 112 longitudinally on the base unit 104. The stylet shaft 124 has a proximal end that is attached to a stylet carrier 220 that is slidably mounted on the base 204. The stylet carrier 220 translates the stylet 110 longitudinally on the base 204. In combination with the cannula carrier 210, the stylet carrier 220 also translates the stylet 110 relative to the cannula 112. The motor 206 includes a drive shaft 221 to which is attached a drive screw 222. The drive screw 222 is threaded through a screw-driven slide 224 that moves the cannula carrier 210 and the stylet carrier 220 in the manner described below.

The stylet 110 and the cannula 112 are preferably separable from the stylet carrier 220 and the cannula carrier 210, respectively. In this way, the entire probe unit 102, including the stylet 110 and cannula 112, may be replaced upon each use, without having to replace the entire device. This allows the stylet 110 and cannula 112 to be disposable, so that a new, sterile stylet and cannula may be used for each biopsy procedure.

The proximal end of the stylet 110 may be embedded in or attached to a stylet foot 225, formed of an electrically insulating material, such as plastic. The stylet foot 225 is removably mounted in the stylet carrier 220. For example, the stylet foot 225 may fit into a correspondingly shaped recess in the stylet carrier 220. A stylet retention strip 227, having its two ends removably attached to the stylet carrier 220, and extending across the top of the stylet foot 225, retains the stylet foot 225 in the stylet carrier 220.

Similarly, the proximal end of the cannula 112 may be embedded in or attached to a cannula foot 229, formed of an electrically insulating material, such as plastic. The cannula foot 229 is removably mounted in the cannula carrier 210, such as by being retained in a correspondingly shaped recess in the cannula carrier 210. A cannula retention strip 231, having its two ends removably attached to the cannula carrier 210, and extending across the cannula foot 229, retains the cannula foot 229 in the cannula carrier 210.

The entire probe unit 102, including the stylet 110 and the cannula 112 may be made available to medical doctors and hospitals as a single modular unit, ready for attachment to the base unit 104. In this way, the sterility of the probe unit 102 may be maintained. After completion of a biopsy procedure, the entire probe unit 102 may then be removed from the base unit 104 and discarded in accordance with proper procedures for medical waste.

Figure 7:
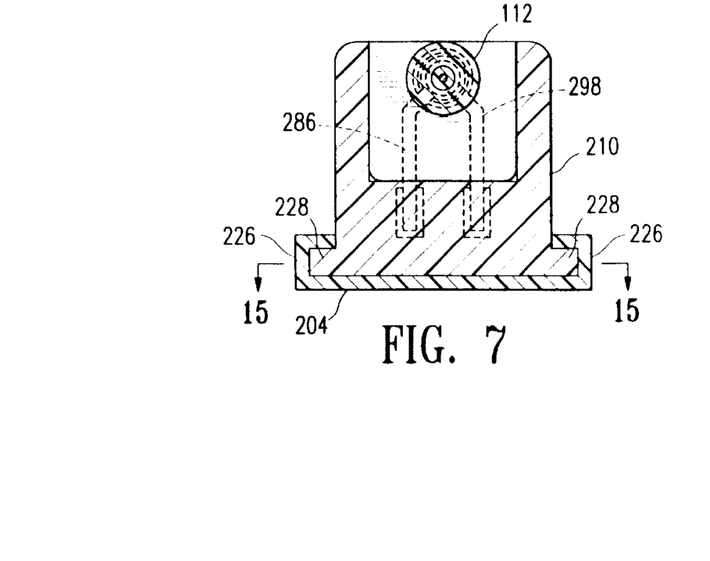
FIG. 7 is a cross-sectional view taken along line 7—7 of FIG. 6.

An exemplary mounting for the cannula carrier 210 on the base 204 is illustrated in FIG. 7. The base 204 includes substantially U-shaped channels 226 along each side thereof Horizontal extensions 228 of the bottom portion of the cannula carrier 210 engage these channels 226. The mounting of the cannula carrier 210 on the base 204 preferably provides very little friction between the cannula carrier 210 and the base 204. A low friction mounting helps to ensure smooth and accurate movement of the cannula carrier 210 relative to the base 204.

Figure 8:
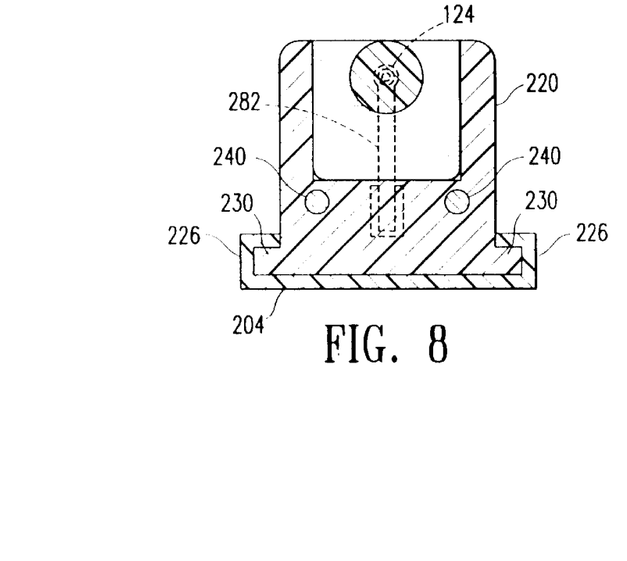
FIG. 8 is a cross-sectional view taken along line 8—8 of FIG. 6.

The mounting of the stylet carrier 220 on the base 204 is advantageously similar to the mounting of the cannula carrier 210. An exemplary mounting for the stylet carrier 220 on the base 204 is illustrated in FIG. 8. Horizontal extensions 230 of the bottom portion of the stylet carrier 220 engage the U-shaped channels 226 formed in the base 204. The mounting of the stylet carrier 220 on the base 204 preferably provides very little friction between the stylet carrier 220 and the base 204. A low friction mounting helps to ensure smooth and accurate movement of the stylet carrier 220 relative to the base 204.

The base 204 includes a plurality of stops that define the maximum extent of the longitudinal movements of the cannula carrier 210 and the stylet carrier 220 along the base 204. In the particular embodiment illustrated, an end piece 232 is provided at the distal end of the base 204. The end piece 232 forms a forward stop for the cannula carrier 210. An intermediate stop 234 is affixed to the base 204. The distal side of the intermediate stop 234 forms a rearward stop for the cannula carrier 210, while the proximal side of the intermediate stop 234 forms a forward stop for the stylet carrier 220. A back stop 236 is affixed to the base 204 as a rearward stop for the stylet carrier 220.

Figure 4:
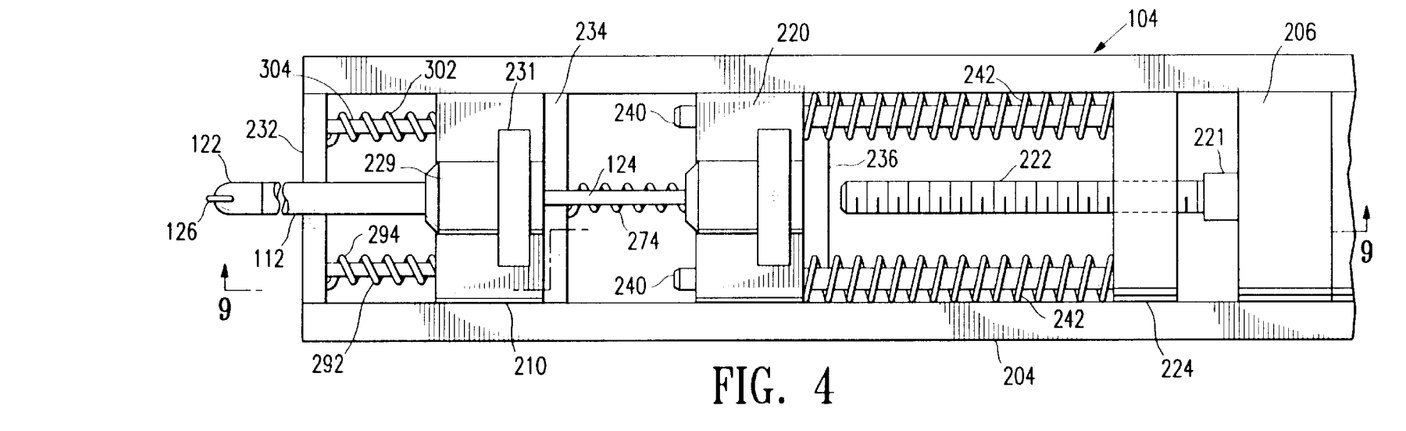
FIG. 4 is a top view of the device of FIG. 1, with the device set to begin a biopsy procedure in accordance with the method of the present invention.
Figure 5:
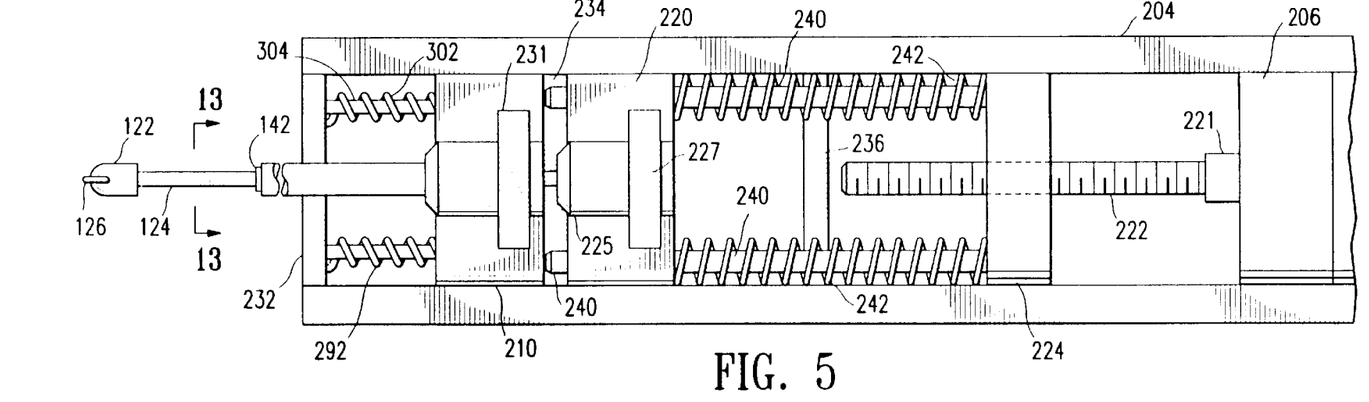
FIG. 5 is a second top view, similar to the view of FIG. 4, of the device of FIG. 1, with the stylet extended for an intermediate step of a biopsy procedure in accordance with the method of the present invention.
Figure 6:
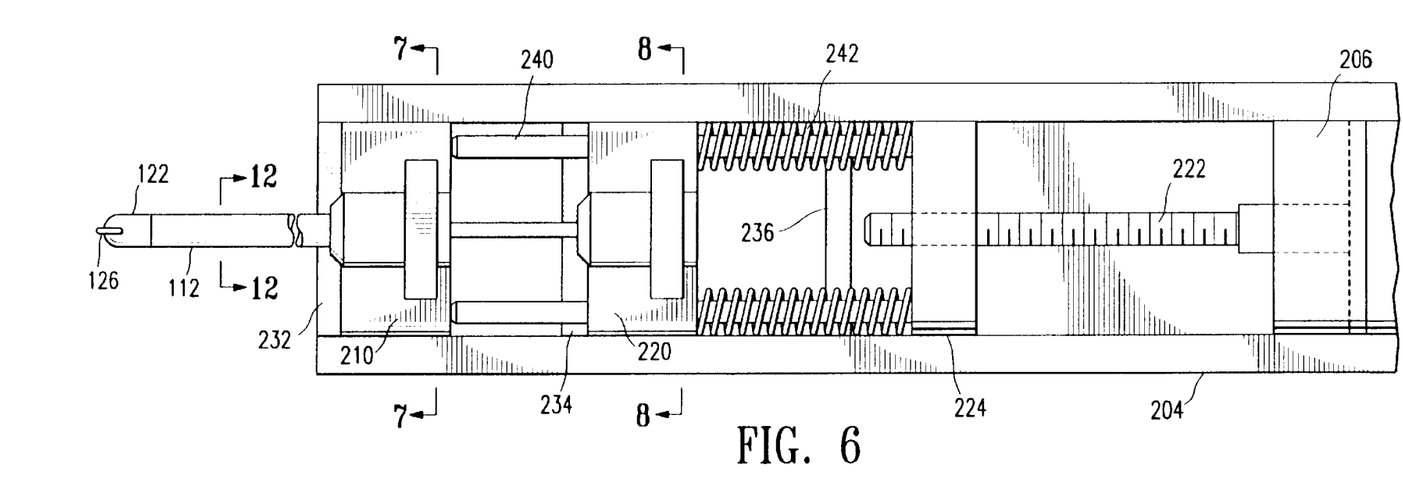
FIG. 6 is a third top view, similar to the view of FIG. 4, of the device of FIG. 1, with both the stylet and the cannula extended for a further stage of a biopsy procedure in accordance with the method of the present invention.

The cannula carrier 210 may be moved between a withdrawn position (illustrated in FIGS. 4 and 5) and an extended position (illustrated in FIG. 6). In the withdrawn position, the distal edge of the cannula carrier 210 is spaced from the end piece 232 of the base 204, and the proximal edge of the cannula carrier 210 abuts against the distal side of the intermediate stop 234. In this withdrawn position, the cannula 112 is withdrawn relative to the base 204. When the cannula carrier 210 is in the extended position, the distal edge of the cannula carrier 210 abuts against the end piece 232, and the cannula 112 is extended distally with respect to the base 204. As the cannula carrier 210 moves toward the distal end of the base 204, the cannula 112 moves distally with respect to the base 204. As the cannula carrier 210 moves toward the proximal end of the base 204, the cannula 112 moves proximally with respect to the base 204.

The stylet carrier 220 may also be moved between a withdrawn position (illustrated in FIG. 4) and an extended position (illustrated in FIGS. 5 and 6). In the withdrawn position, the distal edge of the stylet carrier 220 is spaced from the intermediate stop 234, and the proximal edge of the stylet carrier 220 abuts against the back stop 236. In this withdrawn position, the stylet 110 is withdrawn relative to the base 204. When the stylet carrier 220 is in the extended position, the distal edge of the stylet carrier 220 abuts against the proximal side of the intermediate stop 234. As the stylet carrier 220 moves longitudinally on the base 204 toward the distal end of the base, the stylet 110 moves distally with respect to the base 204. As the stylet carrier 220 moves longitudinally on the base 204 toward the proximal end of the base, the stylet 110 moves proximally with respect to the base 204.

A drive mechanism on the base 204 moves the cannula carrier 210 and the stylet carrier 220. In the particular embodiment illustrated, the drive mechanism includes the electric motor 206, the drive screw 222, and the screw-driven slide 224. The screw-driven slide 224 is slidably mounted on the base 204 so as to be movable between a proximal position in which it is relatively near the motor 206, and a distal position in which the it is relatively remote from the motor 206, and nearer the distal end of the base 204. The movement of the screw-driven slide 224 controls the movement of the cannula carrier 210 and the stylet carrier 220.

The screw-driven slide 224 is moved along the base 204 by the drive screw 222, which in turn is driven by the motor 206 by means of the drive shaft 221. The motor 206 rotates the drive shaft 221 and the screw 222, the latter engaging threads (not shown) in the screw-driven slide 224 to move the screw-driven slide 224 along the base 204. When the motor 206 rotates in a first direction (for example, clockwise), the motor turns the drive screw 222 in the same direction, which in turn moves the screw-driven slide 224 from its proximal position toward its distal position. When the motor 206 rotates in the opposite direction, the rotation of the screw 222 moves the screw-driven slide 224 in the opposite direction, toward its proximal position.

A pair of push rods 240 are fixed to the distal side of the screw-driven slide 224. Each of these push rods 240 extends through openings (not shown) in the stylet carrier 220, so that the distal ends of the push rods 240 may engage the proximal side of the cannula carrier 210. A spring bias is provided between the screw-driven slide 224 and the stylet carrier 220. This spring bias tends to maintain a specific predetermined separation between the screw-driven slide 224 and the stylet carrier 220. This spring bias may be provided by a pair of coil springs 242, each of which surrounds one of the push rods 240.

The mechanical operation of the base unit 104 will now be described with reference to FIGS. 4, 5, and 6. Referring first to FIG. 4, the biopsy device is illustrated in a configuration in which it is set to begin a biopsy procedure. The stylet 110 is withdrawn relative to the cannula 112 so that the stylet 110 abuts against the distal end of the cannula 112. The cannula 112 and stylet 110 are both withdrawn to the full extent possible relative to the base 204; that is, they are at their respective proximal limits of travel relative to the base 204.

As the motor 206 is operated, it turns the screw 222, which moves the screw-driven slide 224 toward the distal end of the base 204 in the manner described above. The springs 242 between the screw-driven slide 224 and the stylet carrier 220 maintain the predetermined spacing between the screw-driven slide 224 and the stylet carrier 220, thus causing the stylet carrier 220 to move toward the distal end of the base 204 at approximately the same rate as the screw-driven slide 224. However, the cannula carrier 210 remains in its original position. Thus, the stylet 110 extends distally relative to the cannula 112, so that the stylet head 122 separates from the distal end of the cannula 112. This continues until the distal ends of the push rods 240 contact the proximal side of the cannula carrier 210, as illustrated in FIG. 5. At this stage, the stylet head 122 is spaced from the distal end of the cannula 112, forming a gap between the proximal end of the stylet head 122 and the distal end of the cannula 112.

Also at this stage, the distal side of the stylet carrier 220 contacts the proximal side of the intermediate stop 234, blocking further movement of the stylet carrier 220 toward the distal end of the base 204. As the motor 206 continues to rotate the drive screw 222, it continues to move the screw-driven slide 224 toward the distal end of the base 204. However, further movement of the stylet carrier 220 is blocked. As the spring bias provided by the springs 242 is overcome, the springs 242 compress, and the screw-driven slide 224 moves closer to the stylet carrier 220. As the screw-driven slide 224 moves close to the stylet carrier 220, the push rods 240 extend from the distal side of the stylet carrier 220 and engage the proximal side of the cannula carrier 210. As the screw-driven slide 224 continues to move toward the distal end of the base 204, the push rods 240 move the cannula carrier 210 toward the distal end of the base 204. This forward (distal) movement of the cannula carrier 210 moves the cannula 112 relative to the stylet 110, closing the gap between the stylet head 122 and the distal end of the cannula 112, so that the stylet 110 is withdrawn relative to the cannula 112.

When the distal end of the cannula 112 contacts the proximal end of stylet head 122 (as illustrated in FIG. 6), further forward (distal) movement of the cannula carrier 210 should be stopped. Forward movement of the cannula carrier 210 toward the distal end of the base 204 may be stopped by stopping the motor 206. The components of the device, including the base 204 and the stops 232, 234, 236, may also be dimensioned so that at that point the distal side of the cannula carrier 210 contacts the end piece 232 of the base to stop further movement of the cannula carrier 210 in the distal (forward) direction.

As noted previously, the energy for the stylet electrode 126 and the cannula electrode 142 is supplied by the RF generator 106. Furthermore, the control of activation of the electrodes 126, 142, as well as control of the motor 206 that moves the cannular carrier 210 and the stylet carrier 220, is provided by the control unit 108. Accordingly, electrical paths must be provided to conduct energizing current through the base unit 104 from the RF generator 106 to the stylet electrode 126 and the cannula electrode 142, and to conduct control signals from the control unit 108 to the motor 206. (Control signals are also sent from the control unit 108 to the RF generator 106 to control the activation of the electrodes 126, 142.) In addition, a return electrical path must be provided for the patient return pad 150 (monopolar configuration) or the return electrode 152 (bipolar configuration).

Figure 15:
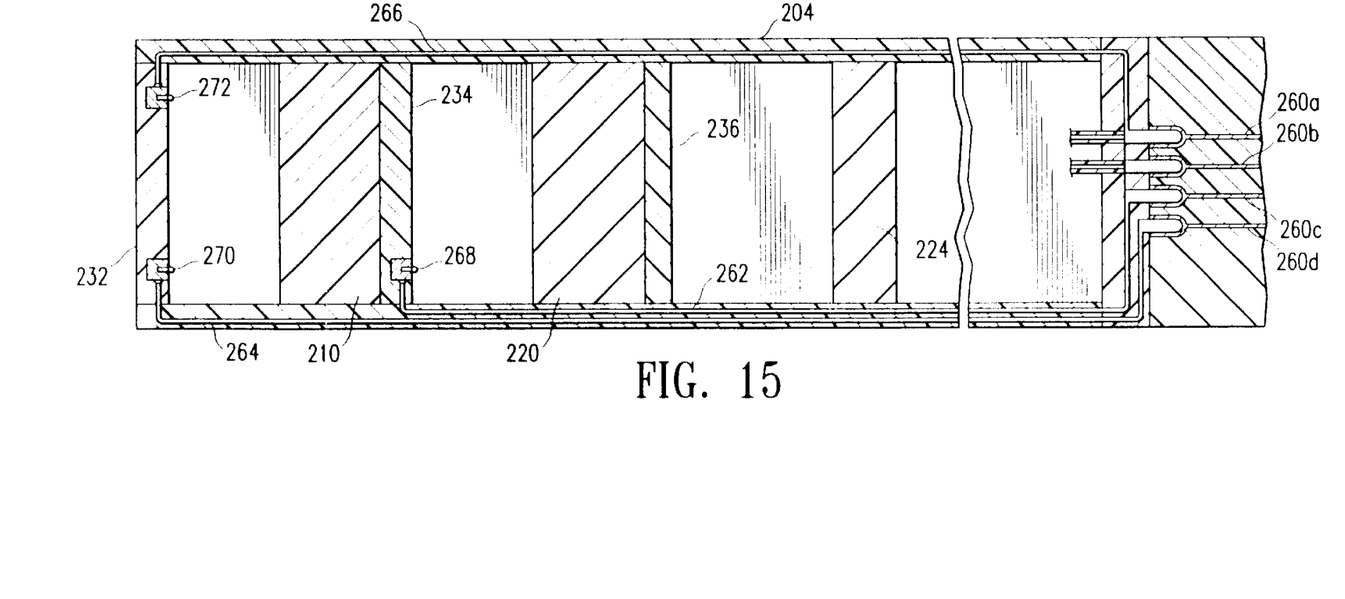
FIG. 15 is a cross-sectional view of the base of the biopsy device, taken along line 15—15 of FIG. 7.

Referring now to FIG. 15, the base 204 includes a plurality of electrical connectors 260a, 260b, 260c, 260d for providing electrical connection to the RF generator 106 and the control unit 108, and to the power supply 207 for the motor 206. A stylet lead 262, a cannula lead 264, and (in a bipolar configuration only) a return lead 266 each have a first end that is internally connected to separate ones of the connectors 260a–d. The other end of the stylet lead 262 is connected to a stylet base contact 268 that is fixed with respect to the base 204. For example, the stylet base contact 268 may be embedded in the intermediate stop 234. Similarly, the other end of the cannula lead 264 is connected to a cannula base contact 270 that is fixed with respect to the base 204. For example, the cannula lead contact 264 may be embedded in the base end piece 232.

The return lead 266 is included only in the bipolar configuration. It is not necessary in the monopolar configuration that includes the remote patient return pad 150 (FIG. 1). In the monopolar configuration, the connection between the patient return pad 150 and the RF generator and control unit 106 may be provided externally to the base unit 104. The return lead 266 in the bipolar configuration may be connected to a cannula return base contact 272 that is fixed with respect to the base 204. For example, the return base contact 272 may also be embedded in the base end piece 232.

Figure 9:
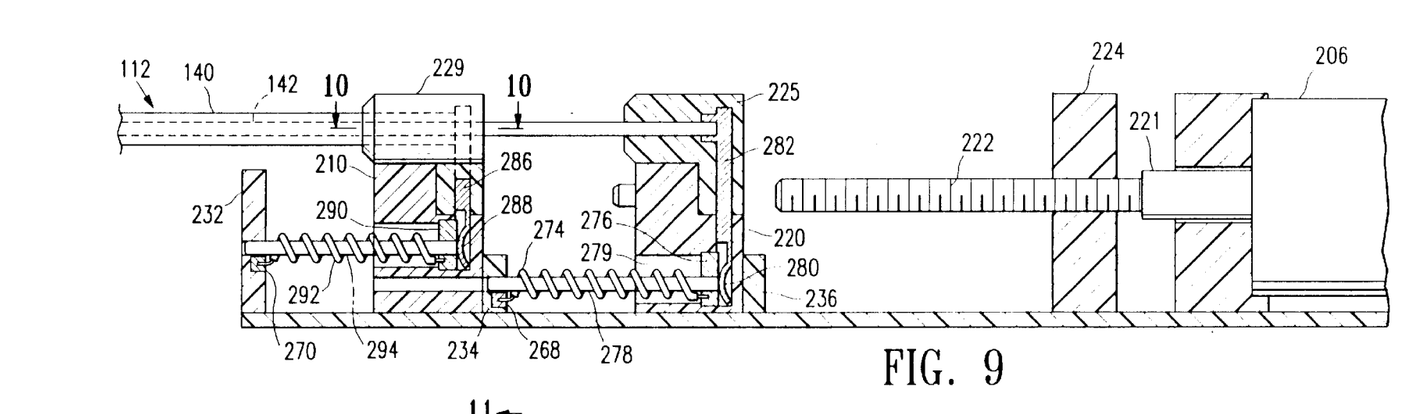
FIG. 9 is a staggered cross-sectional view taken along line 9—9 of FIG. 4.

Referring next to FIG. 9, the structure of the proximal ends of the stylet 110 and the cannula 112, and the electrical paths for the stylet conductor 128 and for the cannula conductor 144, are illustrated. Referring first to the electrical path for the stylet 110, the stylet base contact 268 is provided in the intermediate stop 234. A stylet wire 274 provides an electrical current path between the stylet base contact 268 and a stylet carrier contact 276 on the stylet carrier 220. Because the position of the stylet carrier 220 changes with respect to the intermediate stop 234, the stylet wire 274 should be able to accommodate changes in the physical separation between the stylet carrier 220 and the intermediate stop 234 while maintaining a connection between the stylet base contact 268 and the stylet carrier contact 276. For example, the stylet wire 274 may be a coiled wire wrapped around a longitudinal pin 278. An opening 279 may be provided in the distal side of the stylet carrier 220 to accommodate the coiled stylet wire 274.

The stylet carrier contact 276 remains in contact with an extension portion 280 of a stylet carrier terminal 282 that is mounted in the stylet foot 225. The stylet carrier terminal 282, in turn, is in electrical contact with the stylet electrical conductor 128 (see FIGS. 12 and 13) that is enclosed in the stylet shaft 124. The stylet carrier terminal extension portion 280 may be formed as a spring to help maintain contact between the stylet carrier terminal extension portion 280 and the stylet carrier contact 276. The stylet carrier terminal 282 (with the extension portion 280) is fixed within the stylet foot 225, so that when the stylet foot 225 is removed from the stylet carrier 220, the stylet carrier terminal 282 (with the extension portion 280) is removed with the stylet foot 225. The extension portion 280 fits through an opening in the stylet carrier 220 so that the extension portion may contact the stylet carrier contact 276.

Figure 10:
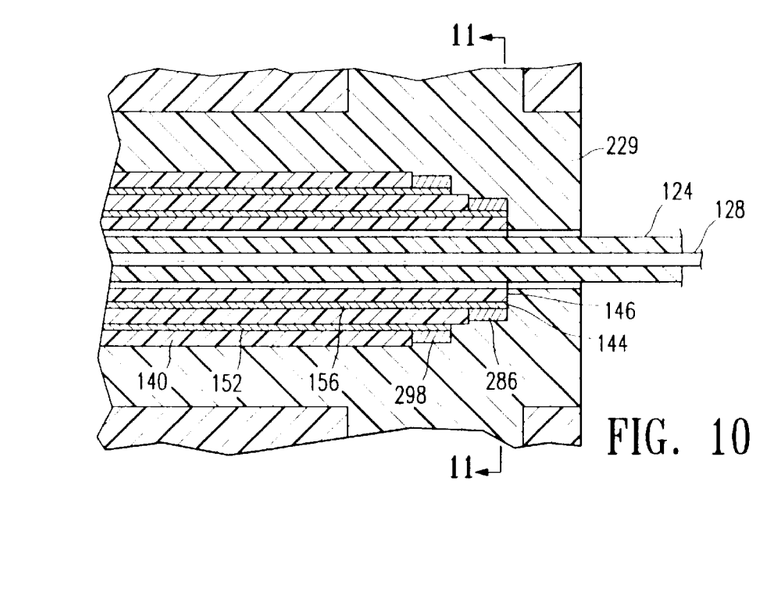
FIG. 10 is a cross-sectional view taken along line 10—10 of FIG. 9.

A similar type of electrical path is provided for the cannula conductor 142 that is contained in the cannula 112. A cannula carrier terminal 286 is fixed within the cannula foot 229, which is removably mounted in the cannula carrier 210, as previously described. The cannula carrier terminal 286 is in electrical contact with the cannula conductor 144 that is enclosed within the cannula tube 140. (See also FIG. 10.) The cannula carrier terminal 286 has a spring extension portion 288 that is in contact with a cannula carrier contact 290 when the cannula foot 229 is mounted in the cannula carrier 210. A cannula wire 292 provides an electrical current path between the cannula carrier contact 290 with the cannula base contact 270 that is embedded in the base end piece 232. Again, because the position of the cannula slide 210 changes with respect to the base end piece 232, the cannula wire 292 is advantageously a coiled wire wrapped around a longitudinal pin 294.

Figure 11:
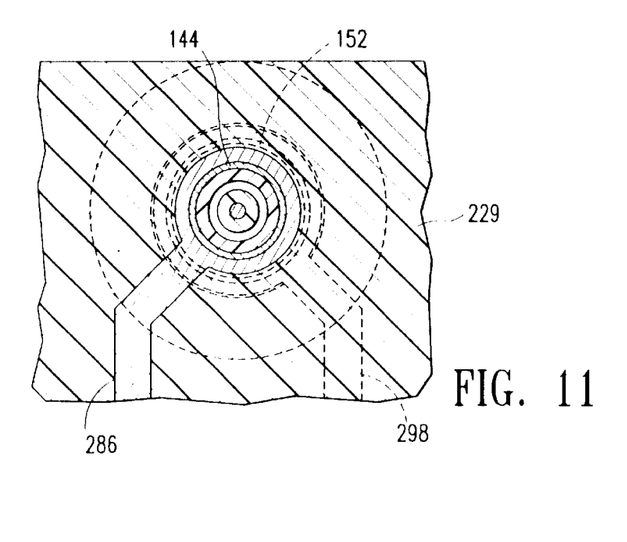
FIG. 11 is a cross-sectional view taken along line 11—11 of FIG. 10.

A series of electrical contacts and electrical wires substantially similar to those for providing the electrical current path for the cannula conductor 144 may be provided in the bipolar configuration in which a return electrode 152 is included in the cannula 112. For example, the return electrical path may be included on the opposite side of the cannula carrier 220 for providing contact between the cannula return electrode 152 and the return base contact 272 that is embedded in the base end piece 232. A return electrode 298 embedded in the electrically insulating cannula foot 229 (FIGS. 10 and 11) provides a portion of such electrical contact. A coiled return wire 302 (FIGS. 4 and 5) provides an electrical current path between the return electrode 298 and the return base contact 272 embedded in the base end piece 232. The coiled return wire 302 may be wrapped around a supporting longitudinal pin 304.

Figure 18:
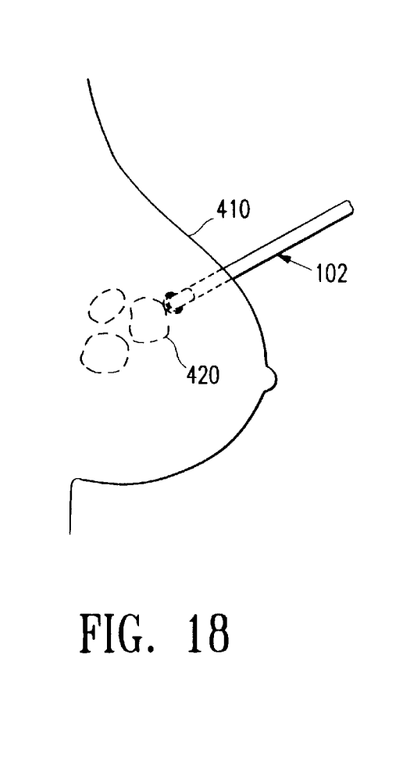
FIG. 18 illustrates the step of inserting the biopsy device into tissue for extracting a tissue specimen, in accordance with the method of the present invention.
Figure 19:
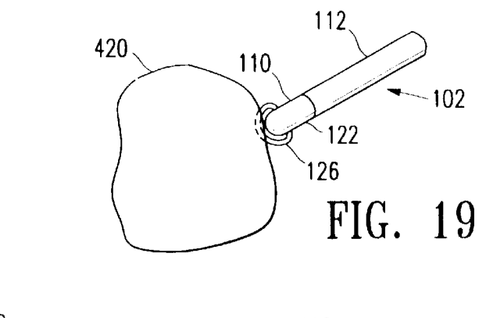
FIG. 19 illustrates the biopsy device positioned to begin extracting a tissue specimen in accordance with the method of the present invention.
Figures 20, 21:
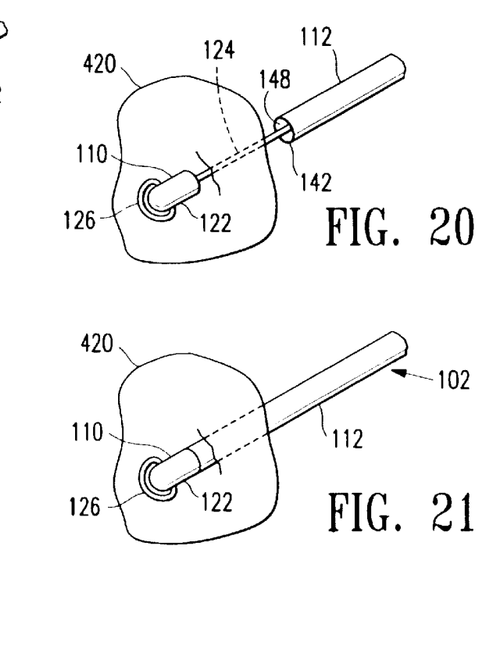
FIG. 20 illustrates the biopsy device at an intermediate step of the biopsy procedure in accordance with the method of the present invention.
FIG. 21 illustrates the biopsy device at a later intermediate step of the biopsy procedure in accordance with the method of the present invention.

A method of performing a biopsy in accordance with an aspect of the present invention will be described with reference to FIGS. 18 through 21. Referring first to FIG. 18, a portion of human tissue, such as a human breast 410, is illustrated containing several tissue masses 420, which may be suspected tumors or lesions to be examined. Through an incision in the tissue 410, the portion of the biopsy probe 102 containing the stylet 110 and the distal end of the cannula 112 is inserted, using RF current, until the stylet head 122 is near a targeted tissue mass 420. The probe 102 is guided toward the targeted tissue mass 420 using conventional imaging techniques, such as ultrasound or X-rays. The stylet 110 and the cannula 112 are both in their withdrawn (proximal) positions, as illustrated in FIG. 4. Insertion of the probe 102 toward the targeted tissue mass 420 may be assisted by energizing the stylet electrode 126 to ablate subcutaneous tissue between the skin and the targeted tissue mass 420. As shown in FIG. 19, while the probe 102 is being inserted to access the targeted tissue mass 420, the stylet 110 is in its withdrawn position relative to the distal end of the cannula 112, so that stylet head 122 abuts or substantially abuts the distal end of the cannula 112, closing the opening in the distal end of the cannula 112, and thus the passage 148.

The stylet electrode 126 is then electrically activated to ablate the tissue of the targeted tissue mass 420. The stylet head 122 is then pushed through the tissue mass 420, creating an opening through the tissue mass 420 as the stylet 110 penetrates the tissue mass by moving distally toward its extended position, while the cannula 112 remains in its proximal position, so that the stylet head 122 separates from the distal end of the cannula 112. A gap is thus opened between the stylet head 122 and the distal end of the cannula 112. A portion of the tissue mass 420 fills in this gap between the stylet head 122 and the cannula 112, around the stylet shaft 124. A particular advantage of the arcuate stylet electrode 126 is that it creates a narrow "slice" through the targeted tissue mass 420, thereby facilitating the filling of the aforesaid gap with the portions of the tissue mass on either side of the "slice" that collapse into the gap after being pushed outwardly by the passage of the stylet head 122.

The stylet electrode 126 may then be deactivated, and the cannula electrode 142 activated. With the cannula electrode 142 activated, the portion of the tissue mass 420 adjacent the cannula electrode 142 is ablated, and the cannula 112 may be pushed forward through the portion of the tissue mass 420 that has filled in around the stylet shaft 124. As the cannula 112 moves through the tissue mass 420, it cuts off a portion of the tissue mass 420, and encases that portion in the annular channel 148 within the cannula 112. Once the cannula 112 has closed the gap between the distal end of the cannula 112 and the stylet head 122, the severed portion of the tissue mass 420 is contained within the annular channel 148 of the cannula 112. The entire probe 102 may then be removed from the tissue mass 420 and the patient's body. Once removed, the cannula 112 and the stylet 110 may again be separated, and the tumor portion contained within the annular channel 148 of the cannula 112 removed for examination and analysis.

Using the device and method of the present invention, the removal of tissue specimens may proceed at a slower pace than is typically possible using conventional spring-activated knife cutters. In particular, additional time can be allowed between the insertion of the stylet through the suspicious tissue, and the insertion of the annular cannula. This additional time allows more of the tissue to fill the space surrounding the stylet shaft 124, allowing the cannula electrode 142 to cut a larger sample of the suspicious tissue than has typically been possible using the cutters of the prior art. In addition, the stylet and cannula of the present invention are less likely to be deflected as they move through the tissue then are the mechanical cutters of prior art biopsy devices.

The specific embodiments described and illustrated above are exemplary, and not exhaustive or exclusive. Those familiar with the art will recognize that various modifications may be made to the specific embodiments described above without departing from the concepts of the present invention. For example, those skilled in the art will recognize that various modifications may be made to the base unit, and that different configurations may be used for controlling the movement and position of the stylet and the cannula. In addition, different specific shapes of the stylet, the stylet head, and cannula may be incorporated into a system implementing the present invention. Furthermore, although an electric motor is the preferred mechanism for driving the cannula carrier and the stylet carrier, other mechanisms, such as mechanical springs or pneumatic mechanisms, may be employed. Indeed, a simplified device may employ manually-driven carriers. Moreover, although RF energy is preferred to effect the tissue ablation, other types of energy (e.g., microwave, ultrasound, or laser) may be employed instead, as mentioned above. These and other modifications and variations that may suggest themselves are considered to be within the spirit and scope of the present invention, as defined in the claims that follow.

What is claimed is:

1. A biopsy system, comprising:
   a) an electrosurgical stylet comprising a shaft having a proximal end, a rounded distal end and a transverse dimension;
   b) a tissue cutting electrode formed of an arcuate length of electrical conductor which is secured to the electrosurgical stylet, which extends over the rounded distal end, which is spaced distally from the rounded distal end and which has a chord length greater than the transverse dimension of the stylet;
   c) a high frequency electrical power source; and
   d) an electrical conductor having a first end electrically connected to said tissue cutting electrode and having a second end electrically connected to the high frequency electrical power source.

2. The biopsy system of claim 1, further comprising a return electrode effective to provide a return electrical path for electrical current from the ablation cutting electrode.

3. The biopsy system of claim 1, wherein said return electrode is contained on the electrosurgical stylet.

4. The biopsy system of claim 1, further comprising a base unit configured to carry the electrosurgical stylet.

5. The biopsy system of claim 4, wherein the base unit has a translation mechanism, a carrier connected to a proximal portion of the stylet mounted on the base unit so as to be movabel on the base unit between a first position in which the stylet is in a withdrawn position and a second position in which the stylet is in an extended position; and a carrier drive, coupled to the carrier, for moving the carrier between the first and second positions.

6. The biopsy system of claim 5, wherein the carrier drive is driven by a motor.

7. The biopsy system of claim 6, wherein the motor has a drive shaft, and wherein the carrier drive comprises a drive screw coupled for rotation with the drive shaft; a screw-driven mechanism coupled between the drive screw and the carrier, whereby rotation of the drive screw in a first direction moves the carrier from the first position to the second position.

8. The biopsy system of claim 4, wherein the base unit is configured to releasably carry the electrosurgical stylet.

9. A tissue accessing system comprising:
   a) an elongated shaft which has a proximal end and a distal end;
   b) a first tissue cutting electrode for accessing a tissue site which is secured to the distal end of the shaft and which has an activatable arcuate portion spaced distally from the distal end of the shaft; and
   c) an electrical conductor which has a first end electrically connected to the tissue cutting electrode and which has a second end electrically connected to a high frequency electrical power source; and
   d) a second tissue cutting electrode which is disposed proximally of said first tissue cutting electrode and in a plane transverse to the axis of said elongated shaft.

10. The tissue accessing system of claim 9, further comprising a return electrode effective to provide a return electrical path for electrical current from said first tissue cutting electrode.

11. The tissue accessing system of claim 10, further comprising a return electrode for accessing a tissue site within a patient.

12. The tissue accessing system of claim 9, wherein the elongated for accessing a tissue site has a base unit to carry the elongated shaft for translating the elongated shaft between withdrawn a position and said extended positions.

13. The tissue accessing system of claim 12, wherein the base unit is configured to releasably carry the elongated shaft.

* * * * *

UNITED STATES PATENT AND TRADEMARK OFFICE
CERTIFICATE OF CORRECTION

PATENT NO. : 6,689,071 B2
DATED : February 10, 2004
INVENTOR(S) : Burbank et al.

It is certified that error appears in the above-identified patent and that said Letters Patent is hereby corrected as shown below:

Column 16,
Line 29, after "tissue cutting electrode and" insert -- which lies --.
Line 40, after "elongated shaft" delete "for translating" and insert -- and a translation mechanism coupled to --.
Line 41, before "between" insert -- for translating the elongated shaft -- and after "between" delete "withdrawn a position and said extended positions" and insert -- a withdrawn position and an extended position --.

Signed and Sealed this

Third Day of May, 2005

JON W. DUDAS
*Director of the United States Patent and Trademark Office*